United States Patent
Van Arman et al.

(10) Patent No.: US 6,915,712 B1
(45) Date of Patent: Jul. 12, 2005

(54) DETECTABLE SAMPLING ARRANGEMENT

(75) Inventors: John Van Arman, Easton, PA (US); Jackie Swartzberg, Oakland, NJ (US); David Landsberger, Caldwell, NJ (US); Francis Gomes, Jersey City, NJ (US)

(73) Assignee: Bel-Art Products, Inc., Pequannock, NJ (US)

( * ) Notice: Subject to any disclaimer, the term of this patent is extended or adjusted under 35 U.S.C. 154(b) by 457 days.

(21) Appl. No.: 10/237,157

(22) Filed: Sep. 6, 2002

(51) Int. Cl.[7] .............................................. G01N 1/00
(52) U.S. Cl. ........................................................ 73/863
(58) Field of Search .............................. 73/863, 864.91

(56) References Cited

U.S. PATENT DOCUMENTS

| | | | | |
|---|---|---|---|---|
| 3,942,023 A | * | 3/1976 | Flaugnatti | 250/515.1 |
| 4,020,152 A | * | 4/1977 | Heitz | 424/9.411 |
| 4,103,176 A | * | 7/1978 | Coyle | 378/204 |
| 4,181,859 A | * | 1/1980 | Vitalini | 378/164 |
| 4,748,915 A | * | 6/1988 | Hastings et al. | 109/2 |
| 4,766,420 A | * | 8/1988 | Hastings et al. | 340/550 |
| 4,837,795 A | * | 6/1989 | Garrigus | 378/180 |
| 5,054,327 A | * | 10/1991 | Gould | 73/863 |
| 5,383,472 A | * | 1/1995 | Devlin et al. | 600/584 |
| 6,009,766 A | * | 1/2000 | Solazzi | 73/864.91 |
| 6,440,373 B1 | | 8/2002 | Gomes et al. | |
| 6,568,398 B2 | * | 5/2003 | Cohen | 128/898 |
| 6,779,410 B2 | * | 8/2004 | Koo et al. | 73/863 |
| 2002/0184748 A1 | * | 12/2002 | Heike et al. | 29/469.5 |

FOREIGN PATENT DOCUMENTS

JP 63153458 A * 6/1988 ........ G01N 23/223

OTHER PUBLICATIONS

Lightek Corp., Radiopaque Solutions, Internet Publication.*
CIRS, Specimen Imaging and Transport Chamber, Internet publication.*
Wilson et al., "The ratio-opacity of surgical and radiological devices used in vivo: a test method for markers in surgical gauze," Phys. Med. Biol., vol. 32, No. 10, 1283-1289.*
Bel-Art Products, Catalog 198, pp. 381-399.
Bel Art Products, Sample Collection and Handling Tools Catalog.

* cited by examiner

Primary Examiner—Hezron Williams
Assistant Examiner—John Fitzgerald
(74) Attorney, Agent, or Firm—Lawrence G. Fridman

(57) ABSTRACT

A detectable device for collecting samples consists of a collecting scoop and a handle extending outwardly therefrom. The detection of the device is improved by uniformly dispersing at least one radio-opaque substance within a dispersing medium of its material.

11 Claims, 1 Drawing Sheet

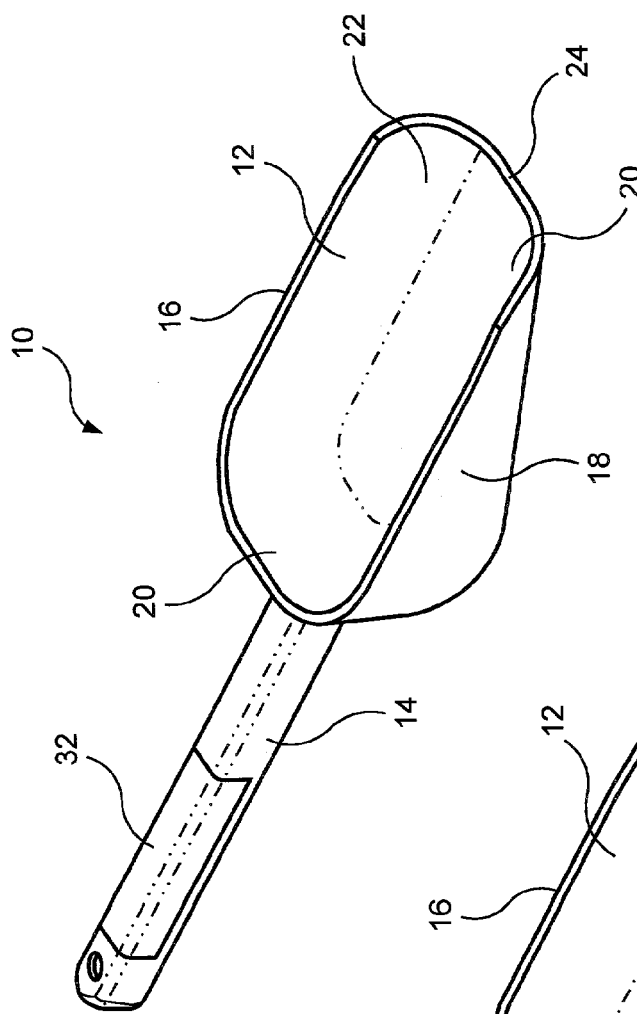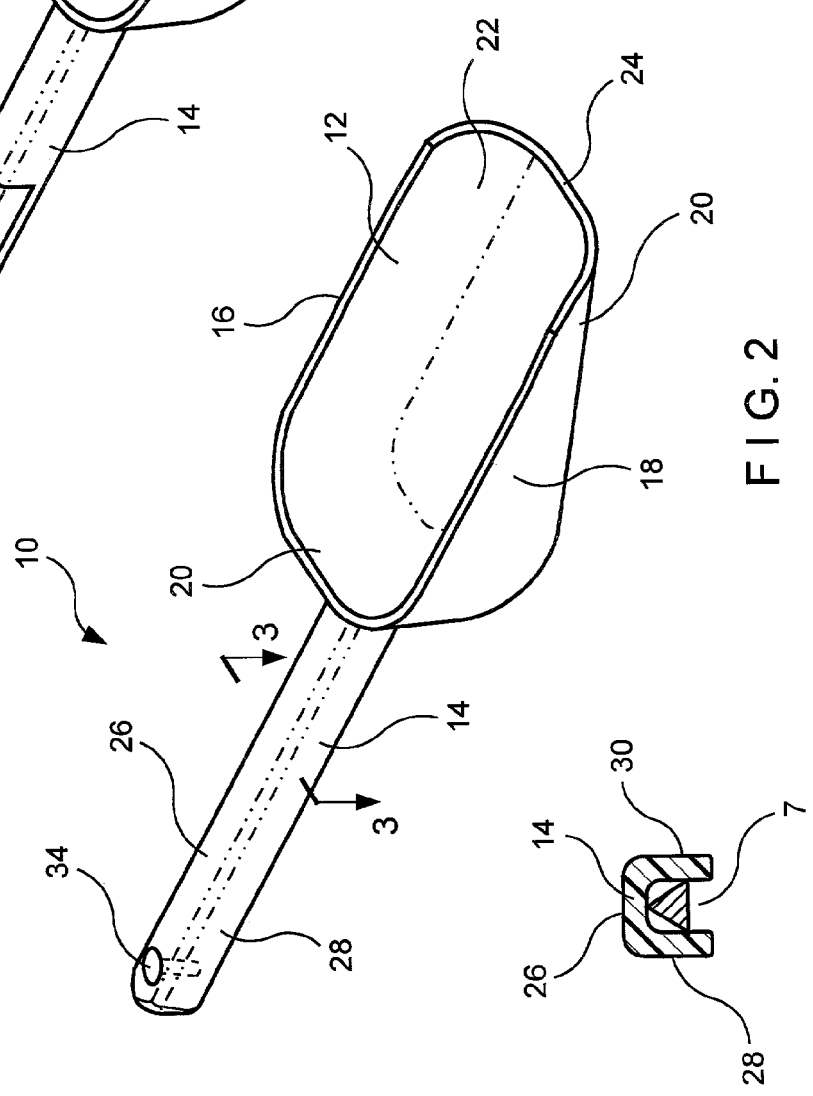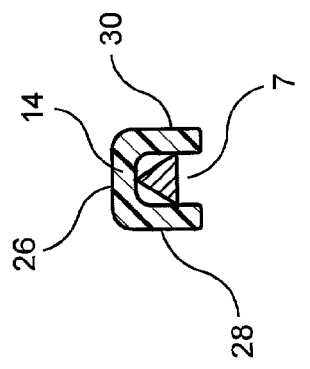

DETECTABLE SAMPLING ARRANGEMENT

BACKGROUND OF THE INVENTION

1. Field of the Invention

This invention relates to collecting samples, and more particularly to a detectable sampling device having a detectable element as an integral part of its structure.

2. Description of the Background and Prior Art

In food, pharmaceutical, environmental, dairy, cosmetic, and other industries sampling of materials or products has to meet requirements of FDA, EPA, USDA and other government agencies.

Among the factors to consider in determining a suitable equipment used for sampling collection are: the type materials being sampled, the frequency of sampling and the sample's location. The sampling devices should not contain elements or materials that may contaminate the sample. The sampling devices should have a smooth surface with no adhesive quality and should be easily cleaned as well as sterilizable, if necessary.

Among most common sample collection techniques are the multi-layer and target sampling. With the multi-layer technique, a single sample is taken through all the material layers to obtain an accurate representation of the whole product. In the target sampling, several samples are taken from predetermined areas and averaged together to obtain an accurate representation of the whole product. Both techniques require use of multiple sampling devices.

In each technique there are many steps in the bulk and individual processing before products reach the package stage. Samples are collected at all stages of the processes for quality assurance, microbiological testing and process management. In all of these stages a risk exists that sampling devices or tools can be lost within the tested product ultimately effecting its quality. The addition of x-ray and other detection capabilities increase the safety of the use of sampling tools and prevents contamination of the tested products.

The x-ray inspection of materials and products is gaining acceptance in the above discussed industries. X-ray inspection provides a simple, noncontact method of detecting lost or misplaced sampling devices within the inspected product.

In the typical X-ray and metal detection inspection system, the product is conveyed on a belt and passes through a narrow fan-shaped beam. Below the belt, a multiplicity of individual detectors are provided. The inspected area is repetitively scanned and signals are sequentially sent to a computer to generate an image. The image is then analyzed, and when a decision is made that a sampling device is present in the inspected material, the rejection mechanism is activated.

In the prior art many sample collection devices such as scoops, spoons, etc. are made from materials which are not completely X-ray detectable. Sometimes the sample collection devices are made from a plastic material which is not completely detectable by x-rays and other types of radiation. The images generated by such devices during the inspection procedure are not intensive and dense, so that it is often difficult to identify this device within the bulk of the inspected materials and products and prevent their contamination.

SUMMARY OF THE INVENTION

One aspect of the invention provides a detectable device for collecting samples consisting of a collecting scoop and a handle extending rearwardly therefrom. The collecting scoop includes a pair of spaced side walls integrally joined by a connecting wall, so as to form an open channel adapted to receive a sample during sample collection. Each side wall together with a connecting wall forms a continuous front surface provided at a free end of the collecting scoop. The detection of the device is improved by uniformly dispersing at least one radio-opaque substance within a dispersing medium of its material.

As to another aspect of the invention the radio-opaque substance consists of particles either of barium sulfate or zirconium oxide uniformly distributed within the dispersing medium.

As to a further aspect of the invention the dispersing medium is a polymer plastic or polystyrene and a coloring agent can be added to the dispersing medium.

As to still another aspect of the invention the handle is formed with a continuous C-shaped channel adapted to receive a metal member. A radio-opaque or metal foil is provided on an outer surface of the handle.

BRIEF DESCRIPTION OF THE DRAWINGS

The preferred embodiment of the invention will hereinafter be described in conjunction with the appended drawings which are provided to illustrate and not to limit the invention, and wherein:

FIG. 1 shows a semi-perspective view illustrating one embodiment of the sampling arrangement of the invention;

FIG. 2 is a semi-perspective view illustrating another embodiment of the sampling arrangement of the invention; and FIG. 3 is a cross-section view according to section line 3—3 of FIG. 2.

DETAILED DESCRIPTION OF THE PREFERRED EMBODIMENTS

As illustrated in FIGS. 1 and 2, a sample collection device 10 of the invention includes a scoop 12 and a handle 14 extending rearwardly therefrom.

The scoop includes a pair of spaced side wall portions 16 and 18 that are integrally joined by a connecting wall portion 20 to form an open channel 22 into which the sample is received during sample collection. The side wall portions 16 and 18 can be substantially straight and extend substantially parallel to each other, while the connecting wall portion 20 is curved. In an alternative arrangement, only one side wall can be straight and the side wall portions extend in a non-parallel fashion. The wall portions are arranged to form a continuous front surface 24.

As shown most clearly in FIG. 3, in one embodiment of the invention the longitudinally extending handle 14 is formed with a C-shaped channel 7 which is open at a lower side thereof. The handle also includes upper 26 and side surfaces 28, 30 which can be adapted to receive a label or other detectable elements. Although the handle having an inner C-shaped channel has been illustrated and discussed hereinabove, a handle of other conventional configurations is also contemplated.

The collection device 10 of the invention is preferably molded of a polymer plastic material such as polystyrene or other similar plastics that can be sterilized by gamma-radiation and that exhibits good stiffness in strength to resist forces during the sampling procedure. The coring scoop 12 and handle 14 are preferably integrally molded into a unitary structure during the manufacturing process. However, each part may be formed separately and joined together through ultrasonic welding, adhesive, or other known joining techniques.

As best illustrated in FIG. 1, in one embodiment of the invention the sampling device 10 is formed containing a metal insert 32, which is typically positioned within the handle. This metal insert 32 is easily identifiable by either a metal detection or by the X-ray inspection techniques, producing the images, which are substantially more dense and intensive than the images of a regular plastic itself. As illustrated in FIG. 1, the detectable insert 32 can be provided in the form of a metal-base foil which is, at least partially, wrapped around the handle 14 remotely from the scoop 12. As illustrated in FIG. 2, the detectable member can be in the form of a metal rivet 34 positioned within the body of the handle at the free end thereof.

In the preferred embodiment of the invention, in order to further improve detection, the sampling device 10 is made from a plastic or a dispersing medium in which at least one radio-opaque substance is being dispersed. As often occurs in the prior art, the radiographically-opaque or X-ray detectable substance is not distributed uniformly within a dispersing medium such as a plastic, but in a random fashion. This means that certain parts of the dispersing medium or plastic are rich in the radio-opaque substance, while the other parts contain none of it. In this instance the quality of the visual contrast observed on the X-ray image substantially diminishes. Furthermore, uneven distribution of radio-opaque substances within the dispensing medium tend to reflect or deflect the X-rays. This may cause unsatisfactory radiographs or uncontrolled or blurred exposure produced by X-ray imaging device. Thus, if the material of a sampling device is not uniformly radio-opaque, it may be difficult to locate its position within the bulk of the inspected material.

To enhance the detectability by x-ray imaging apparatus, a material of the sampling arrangement of the invention contains at least one radio-opaque substance provided in the proper quantity and thoroughly mixed with the dispersing medium of the plastic material.

In the sampling device of the invention barium sulfate is typically utilized as a radio-opaque substance used to enhance visualizing the images thereof. Numerous applications confirm the unsurpassed basic suitability of this radio-opaque compound. For practical applications, barium sulfate combine high radiation absorption with other desired qualities. In the present invention the barium sulfate compound is uniformly dispersed or incorporated within the basic plastic material or dispersing medium.

Addition of barium sulfate or other radiographically-opaque substances has the effect of making the sampling device 10 alkali or acid-resistant and of improving its mechanical properties. This means that the plastic materials incorporating barium sulfate are particularly well suited for the manufacturing of sampling devices which are used for sampling of the products having high viscosity, where a substantial force is often required for obtaining of samples.

Although a radio-opaque substance in the form of barium sulfate has been discussed hereinabove, it should be noted that use of other radio-opaque or X-ray detectable compounds is also contemplated for use in the device of the invention. Among such radio-opaque compounds are: zirconium oxide, or other compounds containing barium, zirconium, etc.

In order to further improve the effectiveness of the quality control inspection, the sampling device can be colored. For this reason, during the manufacturing process a coloring agent can be added to the dispensing medium or a plastic material.

The sampling arrangement of the invention can be formed by various state of the art processes, including but not limited to: injection molding, pultrusion, compression, transfer molding, or a combination of these processes.

As indicated hereinabove, in the preferred embodiment, the sampling device of the invention is made from a plastic material. In order to make the x-ray image more intensive and dense, at least one radio-opaque substance, such as, for example, barium sulfate is added to the dispersing medium which is in the form of resin or plastic. Since the sampling device is made from plastic material, it can be easily cleaned and sterilized. Thus, the sampling device is not only detectable by X-rays and other types of radiation, but also generates a more intensive, dense image which makes it easily recognizable during the detection procedure within the bulk of the inspected products and materials.

What is claimed is:

1. A detectable device for collecting samples, the device comprising:
   a collecting scoop and a handle extending rearwardly from the scoop, the collecting scoop including a pair of spaced side walls integrally joined by a connecting wall so as to form an open channel adapted to receive a sample during sample collection, each said side wall together with the connecting wall forming a continuous front surface provided at a free end of the collecting scoop, to thereby facilitate insertion of the scoop into the product;
   whereby detection of the device for collecting samples is improved by uniformly dispersing at least one radio-opaque substance within a dispersing medium of its material.

2. The device of claim 1, wherein said radio-opaque substance consists of particles of barium sulfate finely distributed within said dispersing medium.

3. The device of claim 1, wherein said radio-opaque substance consists of particles of zirconium oxide finely dispersed within said dispersing medium.

4. The device of claim 1, wherein said radio-opaque substance is uniformly dispersed within the dispersing medium forming said collecting scoop and handle.

5. The device of claim 1, wherein said dispersing medium further comprises a coloring agent.

6. The device of claim 1, wherein said dispersing medium is a polymer plastic.

7. The device of claim 6, wherein said dispersing medium is polystyrene.

8. The device according to claim 1, wherein the handle is formed with a continuous C-shaped channel.

9. The device of claim 8, wherein a metal member is positioned within the C-shaped channel.

10. The device according to claim 8 here, wherein a radio-opaque foil is provided on an outer surface of the handle.

11. The device of claim 10, wherein said radio-opaque foil is a metal base foil.

* * * * *